United States Patent [19]

Comstock et al.

[11] Patent Number: 4,715,053
[45] Date of Patent: Dec. 22, 1987

[54] METHOD FOR MONITORING THE CRYSTALLOGRAPHIC TEXTURE OF METALLIC TUBES BY USE OF X-RAY DIFFRACTION

[75] Inventors: Robert J. Comstock, Penn Township, Westmoreland County; George P. Sabol, Murrysville, both of Pa.

[73] Assignee: Westinghouse Electric Corp., Pittsburgh, Pa.

[21] Appl. No.: 695,115

[22] Filed: Jan. 25, 1985

[51] Int. Cl.$^4$ ........................................... G01N 23/207
[52] U.S. Cl. ........................................ 378/73; 378/71
[58] Field of Search .................... 378/71–73, 378/79–81; 376/245, 458, 900; 250/390 F, 390 H

[56] References Cited

U.S. PATENT DOCUMENTS

| | | | | |
|---|---|---|---|---|
| 2,504,389 | 4/1950 | Brosky | .................. | 378/73 |
| 2,798,163 | 7/1957 | Nishigaki | .................. | 378/73 |
| 3,483,377 | 12/1969 | Borkowski et al. | .................. | 250/374 |
| 3,934,138 | 1/1976 | Bens | .................. | 378/72 |
| 4,095,103 | 6/1978 | Cohen et al. | .................. | 378/72 |
| 4,307,364 | 11/1981 | Goebel | .................. | 378/73 |

FOREIGN PATENT DOCUMENTS 0155019 5/1982 German Democratic Rep. ... 378/71

OTHER PUBLICATIONS

"Micro X-Ray Diffraction Camera . . . Single Microcrystals" by Glas E. Scientific Instruments, 1962, vol. 39.

"Thermal Expansion and Preferred Orientation in Zircaloy", J. J. Kearns, WAPD-TM-472, Nov. 1965.

"The Measurement of Residual Stresses with X-Rays"; J. B. Cohen, M. R. James, and B. A. MacDonald, Naval Research Reviews, Nov. 1978, pp. 1–18.

Primary Examiner—Craig E. Church
Assistant Examiner—John C. Freeman

[57] ABSTRACT

The crystallographic texture of metallic tubular articles is characterized by an X-ray diffraction technique where X-rays are directed onto the surface of the tubular article and diffracted X-rays detected by use of a position-sensitive detector. By effecting relative movement of the tubular article and the X-ray source in both a rotational direction about the axis of the tube and in an axial direction, and measuring intensities from multiple Bragg peaks of the diffracted X-rays from a plurality of locations on the tube, the crystallographic texture of the tube is characterized.

25 Claims, 2 Drawing Figures

METHOD FOR MONITORING THE CRYSTALLOGRAPHIC TEXTURE OF METALLIC TUBES BY USE OF X-RAY DIFFRACTION

BACKGROUND OF THE INVENTION

Zirconium metallic tubes, such as those formed from Zircaloy-2 or Zircaloy-4, are used in nuclear reactor fuel assemblies to contain the nuclear fuel. Such tubes, or cladding, must meet stringent requirements in order to provide reliability of the fuel elements. It is important, therefore, to ensure that cladding variability be maintained within limits that do not lead to unacceptable failure rates of fuel rods. A goal of zero defects in such cladding thus suggests the need for improved process control and inspection techniques to insure that all cladding in a fuel assembly meet predetermined specifications.

In general, a supply of cladding in a fuel assembly is qualified for use by measurement of tube properties on a limited number of specimens. The destructive nature of the measurements precludes total inspection of the cladding and allows the potential use of a limited number of out-of-specification tubes in a fuel assembly.

Current specifications for Zircaloy fuel cladding can include the measurement of the contractile strain ratio (CSR) which is one measure of the mechanical anisotropy of the cladding material. The CSR measurement is destructive and is derived from strain measurements over a two inch gage length in the sample. Such a local measure of mechanical anisotropy requires the assurance that adequate process control is maintained so that the measured CSR is representative of the entire lot of cladding.

Due to the above limitations of the current specifications for mechanical anisotropy, alternate techniques which are compatible with one hundred percent inspection and are sensitive to cladding anisotropy are desirable. Mechanical anisotropy in cladding is controlled by crystallographic texture and thus, a technique which is sensitive to texture variations is a more direct way of ensuring that mechanical anisotropy requirements are met.

While X-ray diffraction is generally regarded as a laboratory technique, technical advances in X-ray tubes and detectors have enabled X-ray diffraction to be performed in a timely manner outside of the laboratory. This is best illustrated by the measurement of residual stresses by X-ray diffraction in the field by portable, hand-held units. Such measurements can be performed in about ten seconds. As examples of such residual stress measurements by X-ray diffraction, reference is made to U.S. Pat. No. 3,934,138 and U.S. Pat. No. 4,095,103, the contents of both said patents being incorporated by reference herein. In U.S. Pat. No. 3,934,138, an instrument is used that incorporates two separate position-sensitive X-ray detectors. Changes in diffraction angle are measured relative to an unstressed first specimen of the same material as the body whose stress is measured, and the instrument is calibrated using a second specimen subjected to a known stress. In U.S. Pat. No. 4,095,103, a quick and precise measurement of residual stress is effected by performing two diffraction angle measurements successively with only a single detector. The measurement is made by positioning an X-ray source to direct a beam toward the principal surface of the test specimen. The X-rays are diffracted by the specimen and the angle of diffraction is measured with a position-sensitive proportional counter, and diffraction peaks located. The X-ray source and detector are rotated by a predetermined angle and a second diffraction peak located. Residual stress is then calculated by applying formulae derived from linear isotropic theory.

It is an object of the present invention to characterize the crystallographic texture of metallic tubes, such as nuclear fuel cladding, by an X-ray diffraction technique.

SUMMARY OF THE INVENTION

The crystallographic texture of metallic tubes is characterized by directing X-rays, at an angle to the surface of the tube, onto the tube, detecting the diffracted X-rays at a spaced location from the tube in a position-sensitive X-ray detector over a predetermined range of scattering angles, and measuring intensities from multiple Bragg peaks of the diffracted X-rays. The tube is moved past the X-ray source and spaced position-sensitive detector, and rotated about its own axis, such that the diffracted X-rays are measured from a plurality of locations on the tube to give the texture, and hence a measure of the mechanical anisotropy of the entire tube.

DETAILED DESCRIPTION

Figure 1:
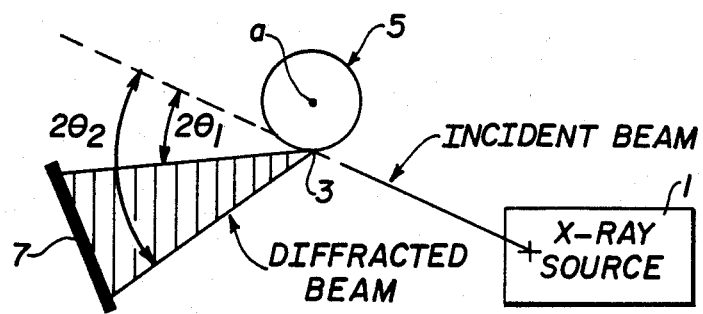
FIG. 1 is a schematic illustration of one embodiment of the present process where the tube is rotated about its axis and is moved in a direction perpendicular to the diffraction plane.

According to the present method, the crystallographic texture of tubular structures is characterized by an X-ray diffraction technique. As is well-known, upon an X-ray striking a crystal, part of the incident energy is absorbed by the crystal, part is transmitted, and part is diffracted, i.e. radiation of the same wavelength as the incident radiation is emitted in directions differing from those of the incident beam. The diffraction conditions are determined by Bragg's law, where $\lambda = 2d \sin \theta$, a law expressing the condition under which a crystal will diffract a beam of X-rays with maximum distinctness. In the formula, $\lambda$ is the wavelength of the X-rays, d is interplaner spacing of the crystal lattice planes, and $\theta$ is the diffraction angle, or Bragg angle. For a fixed X-ray wavelength, typically the characteristic wavelength of the X-ray source, sharp diffraction peaks will occur at several distinct diffraction angles as determined by the several distinct interplaner spacings which are present in crystalline materials.

The integrated intensities of the diffraction peaks are proportional to the number of crystallites which are properly oriented for diffraction. Therefore, by measuring the integrated intensity of a diffraction peak, a measure of the number of crystallites in a particular orientation can be obtained. This procedure is used in the construction of inverse pole figures in which integrated intensities from all measurable diffraction peaks are obtained. This is typically done in a standard $\theta$:$2\theta$ diffraction scan on samples prepared for measurement in the laboratory. Such measurements on zirconium based alloys are typically performed using CUK$\alpha$ radiation in which integrated intensities from eighteen hkil diffraction peaks are obtained over an angular range from 30 degrees to 140 degrees $2\theta$. These intensities can then be used to calculate a texture parameter (J. J. Kearns, WAPD-TM-472, "Thermal Expansion and Preferred Orientation in Zircaloy", November 1965) which is characteristic of the texture of the sample.

The above described procedure is much too time consuming to lend itself to on-line monitoring of texture which has resulted in X-ray diffraction techniques for texture characterization to be regarded as a laboratory procedure. However, an on-line monitoring technique does not necessarily require complete texture characterization but rather only sufficient sensitivity to discriminate between material with acceptable and unacceptable texture. In the proposed X-ray diffraction technique, the peak intensities or integrated intensities from a limited number of diffraction peaks would be measured. For a fixed diffraction geometry, the integrated intensities are proportional to the number of crystallites properly oriented to diffract as well as the incident beam intensity. Ratios of integrated intensities can be calculated to eliminate the dependence on incident beam intensity. Such ratios can then be used to characterize the texture of the material. The number of peaks which have to be measured to ensure adequate sensitivity to texture variations would be determined experimentally for a particular material.

As an example, Table I shows the relative intensities of five diffraction peaks from four samples of tubes formed from Zircaloy-4, the tubes having different texture and hence, different mechanical anisotropy. In Table I, hKil are the Miller indices of the diffracting planes of (A), 0.7" (0.018 meters) outside diameter Zircaloy-4 in an as-pilgered (cold worked) condition; (B), a 0.7" (0.018 meters) outside diameter Zircaloy-4 tube in a recrystallized condition; (C), a 0.7" (0.018 meters) outside diameter tube in a beta-treated condition; and (D), a 0.374" (0.0095 meters) outside diameter tube in a stress relief annealed condition. It is apparent that texture differences between tubes A, B, and C (0.7" diameter tubes of Zirocaloy-4) can readily be established by comparing the intensity ratios of the 0002 and $10\bar{1}1$ peaks. For instances in which there are only small texture differences, comparison of more than two peaks is likely to be required. Once the peaks to be measured have been determined and intensity ratios are established to characterize the desired texture, tubes which statistically deviate from a predetermined specification can be readily identified.

TABLE I

| Relative Integrated Intensities from Four Zircaloy Tubes | | | | |
|---|---|---|---|---|
| hkil | A | B | C | D |
| $10\bar{1}0$ | 10 | 230 | 1320 | 0 |
| 0002 | 1000 | 1000 | 1000 | 1000 |
| $10\bar{1}1$ | 240 | 1520 | 4320 | 160 |
| $10\bar{1}2$ | 130 | 310 | 890 | 140 |
| $11\bar{2}0$ | 710 | 20 | 1330 | 780 |

In order to implement such an inspection technique on all of a set of tubes, rapid integration of multiple Bragg peaks is required. Current technology permits this by use of a position-sensitive detector which enables the diffraction pattern over several degrees $2\theta$ to be simultaneously recorded. This eliminates the need to move a conventional detector over a range of $2\theta$ to measure the diffracted intensity and thus greatly reduces the counting time. A detector with an active length of several inches can be used to detect the diffracted X-rays over a wide angle of scattering angles. The actual range of angles would depend on the length of the detector and the distance of the detector from the tube. A preferred type of position-sensitive detector is that described in U.S. Pat. No. 3,483,377, the contents of which patent are incorporated by reference herein. Such a position-sensitive detector generally has a detector wire which runs along the axis of a gas filled cylinder. An entering X-ray photon creates a pulse in the wire and, by suitable electronics, the location along the wire where the pulse was created can be determined. Measurement of diffraction peaks from a sample of known interatomic spacings enables the location along the wire to be converted to a scattering angle $2\theta$.

In the present process, a source of X-rays directs X-rays of a known characteristic wavelength onto the surface of a metallic tube, the X-rays directed at an angle to the surface of the tube. A position-sensitive detector is positioned in a spaced relation to the tube such that X-rays, diffracted by the tube crystallographic structure, are detected over a range of scattering angles. This range of scattering angles is preferably large anough to include multiple diffraction peaks.

Relative movement between the tube on the one hand, and the X-ray source and position-sensitive detector on the other hand, is effected both in a rotational direction and in an axial direction of the tube. Preferably, the X-ray source and position-sensitive detector are maintained stationary, and the metallic tube is moved past the same in a direction along the axis of the tube and the tube also rotated about its axis. The diffracted X-rays are thus detected from a plurality of locations on the tube.

A schematic illustration of the present X-ray diffraction process for determining anisotropy in a Zircaloy tube is shown in FIG. 1. An X-ray source 1, directs X-rays, at an angle to the surface 3 of a tube 5. The tube axis a is perpendicular to the diffraction plane. Diffracted X-ray beams are collected in a spaced position-sensitive detector 7. The position-sensitive detector records the diffraction pattern in the range of $2\theta_1$ through $2\theta_2$. By using a 4 inch (0.1 meters) long detector 7 and a sample to detector distance of 7.5 inches, (0.19 meters) diffracted intensity over a 30° range in $2\theta$ can simultaneously be recorded and stored in a microprocessor for subsequent peak integrations. This range in $2\theta$ is large enough to include the 5 Bragg peaks in Table I when using CuK$\alpha$ radiation. Additional position-sensitive detectors can be used if peak integrations from Bragg peaks outside this angular range of 30° are required.

While the schematic illustration in FIG. 1 shows diffraction from only one point 3 on the tube 5, by rotating the tube about its axis a and moving the tube in the axial direction perpendicular to the diffraction plane, the diffracted intensity will be collected for the entire tube. This will provide sampling over the entire surface of the tube such that the data reflects the average crystallographic texture of the entire tube. The tube area which is sampled depends on the integrating time, the speed of rotational and axial movement, and the desired statistical counting error. Assuming negligible background intensity, the counting error is given by:

$$\% \text{ Error} = \frac{1}{\sqrt{\text{Integrated Intensity}}} \times 100\%$$

An integrated intensity of 10000 counts is required to achieve 1% error while 400 counts are required for 5% error. This translates into counting times of 200 seconds and 8 seconds, respectively, for a relatively low counting rate of 50 counts/second.

Figure 2:
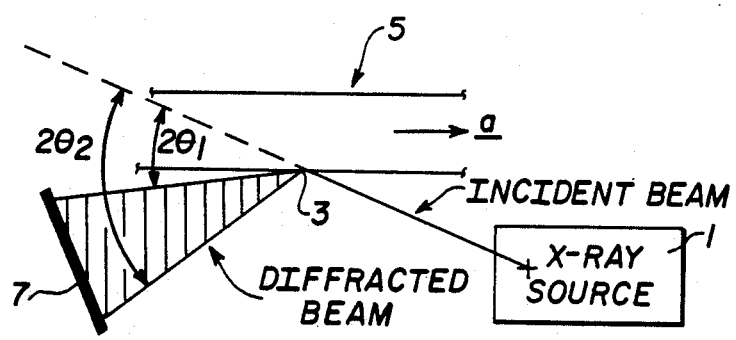
FIG. 2 is a schematic illustration of another embodiment of the present invention where the tube is rotated about its axis and is moved in a direction planar to the diffraction plane.

In FIG. 2, there is schematically illustrated another embodiment wherein the tube axis a of tube 5 is in the diffraction plane, with the tube rotated and moved along its axis planar to the diffraction plane. A diffraction pattern in the range from $2\theta_1$ to $2\theta_2$ is recorded by the position-sensitive detector.

While the above described embodiment uses a measurement of the integrated intensities from multiple Bragg peaks in determining the crystallographic texture of a tube, in some instances, a measurement of the peak intensities alone from a series of multiple Bragg peaks may be sufficient for the purpose of making the desired determination.

The present process is especially useful in monitoring the texture of nuclear fuel cladding that is comprised of zirconium or zirconium alloys containing less than about 5 percent by weight of alloying elements, used in nuclear reactors. The elements that are used in the formation of such alloys include niobium, oxygen, tin, iron, chromium, nickel, molybdenum, copper, vanadium and the like. Especially useful alloys are those known as Zircaloy-2 and Zircaloy-4. Zircaloy-2 contains, by weight, about 1.2–1.7 percent tin, 0.07–0.20 percent iron, 0.05–0.15 percent chromium, and about 0.03 to 0.08 percent nickel, the balance being zirconium, while Zircaloy-4 contains, by weight about 1.2–1.7 percent tin, 0.12–0.18 percent iron, and 0.05 to 0.15 percent chromium, the balance being zirconium.

The present invention provides a process for monitoring the texture of metallic tubes by X-ray diffraction techniques, without the need for destructive testing of a portion of the tube.

What is claimed is:

1. A process for characterizing the crystallographic texture of a surface of a metallic tube, by use of X-ray diffraction, comprising:
   directing X-rays from a source, at an angle to the surface of the metallic tube, onto said metallic tube such that X-rays are diffracted therefrom;
   detecting diffracted x-rays simultaneously over a predetermined range of scattering angles at a spaced location from said metallic tube with an electronic position-sensitive X-ray detector sufficient to detect said X-rays over the predetermined range of scattering angles;
   effecting relative movement between said X-ray source and said metallic tube both in a rotational direction about the axis of the tube and in an axial direction; and
   measuring intensities from multiple Bragg peaks of the diffracted X-rays included in the predetermined range of scattering angles detected by the position-sensitive X-ray detector from a plurality of locations on said tube.

2. The process as defined in claim 1 wherein the relative movement between said X-ray source and metallic tube is effected by rotating said tube about its axis and moving the tube in the direction of the tube axis perpendicular to a diffraction plane, the diffraction plane containing an incident beam by which X-rays are directed from the source to the tube and a diffracted beam by which X-rays are diffracted from the surface to the detector.

3. The process as defined in claim 1 wherein the relative movement between said X-ray source and metallic tube is effected by rotating the tube about its axis and moving the tube in the direction of the tube axis planar to a diffraction plane, the diffraction plane containing an incident beam by which X-rays are directed from the source to the tube and a diffracted beam by which X-rays are diffracted from the surface to the detector.

4. The process as defined in claim 1 wherein the crystallographic texture of the entire tube surface is characterized.

5. The process as defined in claim 1 wherein peak intensities from multiple Bragg peaks are measured.

6. The process as defined in claim 1 wherein integrated intensities from multiple Bragg peaks are measured.

7. The process as defined in claim 1 wherein said metallic tube is formed from a zirconium material selected from the group consisting essentially of zirconium and an alloy of zirconium containing up to about 5 percent by weight of an alloying element.

8. The process as defined in claim 7 wherein said metallic tube is a nuclear fuel cladding.

9. The process as defined in claim 8 wherein said metallic tube is formed from Zircaloy-2.

10. The process as defined in claim 8 wherein said metallic tube is formed from Zircaloy-4.

11. A non-destructive process for characterizing the crystallographic texture of a surface of a metallic tube at predetermined locations by use of X-ray diffraction, said process comprising:
    directing X-rays of a known characteristic wavelength from a source at a predetermined angle to the surface of said metallic tube and onto said metallic tube such that X-rays are diffracted therefrom;
    detecting diffracted X-rays simultaneously over a predetermined range of scattering angles at a predetermined spaced position from said metallic tube with an electronic position-sensitive X-ray detector sufficient to simultaneously detect said X-rays over the predetermined range of scattering angles, the predetermined range of scattering angles being large enough to include more than one Bragg diffraction peak;
    effecting relative movement between said X-ray source and said metallic tube both in a rotational direction about the axis of the tube and in an axial direction to direct X-rays onto said metallic tube at a plurality of locations; and
    measuring intensities from at least two of said Bragg peaks of the diffracted X-rays included in the predetermined range of scattering angles detected at predetermined ones of the plurality of locations on said tube.

12. The process according to claim 11 wherein the relative movement between said X-ray source and said metallic tube is effected by rotating said tube about its axis and moving said tube in the direction of the tube axis.

13. The process according to claim 12 wherein said metallic tube is formed from a zirconium material selected from the group consisting essentially of zirconium and an alloy of zirconium containing up to about 5 percent by weight of an alloying element.

14. The process according to claim 13 wherein the crystallographic texture of the entire tube surface is characterized by measuring intensities from multiple Bragg peaks of the diffracted X-rays detected at each of the plurality of locations on said tube.

15. The process according to claim 14 wherein the peak intensities from multiple Bragg peaks are measured.

16. The process according to claim 15 wherein said metallic tube is a nuclear fuel cladding formed from Zircaloy-2.

17. The process according to claim 15 wherein said metallic tube is a nuclear fuel cladding formed from Zircaloy-4.

18. The process according to claim 14 wherein integrated intensities from multiple Bragg peaks are measured.

19. The process according to claim 18 wherein said metallic tube is a nuclear fuel cladding formed from Zircaloy-2.

20. The process according to claim 18 wherein said metallic tube is a nuclear fuel cladding formed from Zircaloy-4.

21. A non-destructive process for characterizing the crystallographic texture of a surface of a metallic tube by use of X-ray diffraction, said process comprising:

directing X-rays from a source at a predetermined angle to the surface of said metallic tube and onto said metallic tube such that X-rays are diffracted therefrom;

detecting diffracted X-rays simultaneously over a predetermined range of scattering angles at a predetermined spaced position from said metallic tube with an electronic position-sensitive X-ray detector so as to simultaneously detect said diffracted X-rays over the predetermined scattering angle;

effecting relative movement between said X-ray source and said metallic tube both in a rotational direction about the axis of the tube and in an axial direction to direct X-rays onto said metallic tube at a plurality of locations;

measuring intensities of multiple Bragg peaks of said diffracted X-rays detected over the predetermined range of scattering angles at predetermined ones of the plurality of locations of said tube; and comparing said intensities from at least two Bragg peaks measured at a plurality of locations on said tube for determining the texture variation in the tube surface at the plurality of locations.

22. The process according to claim 21 wherein said intensities compared are peak intensities.

23. The process according to claim 21 wherein said intensities compared are integrated intensities.

24. The process according to claim 21 wherein said comparing of said intensities comprises comparing a ratio of peak intensities of two predetermined Bragg peaks.

25. The process according to claim 21 wherein said comparing of said intensities comprises comparing a ratio of integrated intensities of two predetermined Bragg peaks.

* * * * *